(12) United States Patent
O'Hanlon et al.

(10) Patent No.: US 7,246,069 B1
(45) Date of Patent: Jul. 17, 2007

(54) METHOD AND APPARATUS FOR ONLINE HEALTH MONITORING

(75) Inventors: Terrence J. O'Hanlon, Blaire, NE (US); Alan S. Bandes, Cortlandt Manor, NY (US); Mark A. Goodman, Cortlandt Manor, NY (US); Michael F. Osterer, Crawford Street, NY (US)

(73) Assignee: UE Systems, Inc., Elmsford, NY (US)

( * ) Notice: Subject to any disclaimer, the term of this patent is extended or adjusted under 35 U.S.C. 154(b) by 0 days.

(21) Appl. No.: 09/404,269

(22) Filed: Oct. 15, 1999

(51) Int. Cl.
*A61B 5/00* (2006.01)
(52) U.S. Cl. .................. 705/3; 600/528; 600/586
(58) Field of Classification Search ............. 705/2, 705/3; 600/586, 528, 504, 500, 485, 450
See application file for complete search history.

(56) References Cited

U.S. PATENT DOCUMENTS

| | | | |
|---|---|---|---|
| 4,531,527 A | 7/1985 | Reinhold | |
| 4,598,590 A | 7/1986 | Busch-Vishniac | |
| 5,724,968 A | 3/1998 | Iliff | |
| 5,784,635 A | 7/1998 | McCallum | |
| 5,832,448 A * | 11/1998 | Brown | 705/2 |
| 5,868,669 A | 2/1999 | Iliff | |
| 5,910,107 A | 6/1999 | Iliff | |
| 5,913,826 A | 6/1999 | Blank | |
| 5,935,060 A | 8/1999 | Iliff | |
| 5,940,892 A | 8/1999 | Hildebrand et al. | |
| 5,966,692 A * | 10/1999 | Langer et al. | 705/3 |
| 6,246,992 B1 * | 6/2001 | Brown | 705/2 |
| 6,302,844 B1 * | 10/2001 | Walker et al. | 600/300 |
| 2001/0051787 A1 * | 12/2001 | Haller et al. | 604/66 |
| 2002/0019748 A1 * | 2/2002 | Brown | 705/2 |

FOREIGN PATENT DOCUMENTS

| | | |
|---|---|---|
| WO | WO-96/26673 | 9/1996 |
| WO | WO-98/07142 | 2/1998 |
| WO | WO-98/35609 | 8/1998 |
| WO | WO-98/50873 | 11/1998 |
| WO | WO-99/13766 | 3/1999 |

OTHER PUBLICATIONS

Horio et al. "Fetal Monitor for Non-Stress-Test Screening at Home" Jan.-Feb. 1998; 32(1); 39-37 [abstract].*
European Search Report Application No. EP 0097 5290 dated Nov. 11, 2004.
European Patent Office Communication pursuant to Article 96(2) EPC, dated Aug. 21, 2006 for EP Applicaiton 00 975 290.8.

* cited by examiner

*Primary Examiner*—Lalita M. Hamilton
*Assistant Examiner*—Kelly S. Campen
(74) *Attorney, Agent, or Firm*—Darby & Darby (57) ABSTRACT

A method and system for providing online health monitoring and accumulating data from patients worldwide, wherein a database for storing a plurality of health statuses of a plurality of users is established, wherein the database is centrally-accessible from the Internet; data corresponding to a health statistic of a user is received from the user, the data being generated by a health monitoring device; the health statistic is analyzed to determine a health status from the health statistic; the health status is stored in the database; and a population statistic is updated based on the health status and the plurality of health statuses. Such monitoring is particularly useful for both diagnosing and prescribing preventive medical treatment, and is particularly suited for the field of cardiovascular health care.

28 Claims, 4 Drawing Sheets

| Age 54 | Weight 56 | Activity Level 58 | Ethnic Background 60 | Medical History 62 | Family Medical History 64 | Data From Monitoring Device 66 | Determined Cardiovascular Age Factor 68 |
|---|---|---|---|---|---|---|---|
| | | | | | | | |
| | | | | | | | |
| | | | | | | | |
| | | | | | | | |

METHOD AND APPARATUS FOR ONLINE HEALTH MONITORING

FIELD OF THE INVENTION

The instant invention relates generally to an apparatus and method utilizing data processing for a business practice, and relates more specifically to an apparatus and method for use with health care and patient record management.

BACKGROUND OF THE INVENTION

Hypertension, commonly referred to as high blood pressure, is a leading cause of cardiovascular diseases in humans. Each year, cardiovascular diseases, including heart attacks, aneurysm, strokes and atherosclerosis, result in the deaths of tens of thousands of adults in the United States alone.

Hypertension does not manifest itself with symptoms that are readily detectable to its victims. A person who forgoes regular examinations may not realize they have hypertension until it produces one or more of the varieties of life-threatening and/or fatal cardiovascular diseases listed above.

The real tragedy with hypertension is that it is readily treatable by non-invasive means such as medication, physical exercise and a combination of the two. Furthermore, any physiological damage caused by hypertension is largely reversible after detection via the same non-invasive treatments when the condition is detected early and, perhaps, with certain surgical procedures when the condition is not detected early. In any event, detection of the condition provides the key to both saving lives and lowering health care and social costs arising from the prevalence of hypertension.

Recognizing this, the United States government, the health insurance industry, hospitals, physicians and health organizations, such as the American Heart Association, spend millions of dollars annually to raise public awareness, fund research, as well as to detect and treat hypertension. However, recent studies suggest that over 35% of people suffering from hypertension today may be unaware that they are potential victims.

An additional problem arises in that there are no provisions for creating or accessing large databases of current patient data relating to hypertension or other health conditions. Such a database could, among other things, aid researchers in identifying particular groups of people who may be prone to hypertension and could help track the progress of efforts to reduce fatalities resulting from this condition.

There is, therefore, a need for an apparatus and method that would more readily raise individual awareness of hypertension, identify both potential candidates for treatment and those afflicted with the condition, as well as provide a centrally-accessible database available to researchers and physicians for monitoring both individuals and the population at large.

SUMMARY OF THE INVENTION

In order to address and solve certain of the foregoing problems, the instant invention includes a method for compiling health information by means of a computer-controlled apparatus. The method comprises the steps of: (1) establishing a database for storing a plurality of health statuses of a plurality of users, wherein the database is centrally-accessible; (2) receiving, from a user, data corresponding to a health statistic of the user, the data being generated by a health monitoring device; (3) determining a health status of the user from the health statistic; (4) storing the health status in the database; and (5) updating a population statistic based on the health status and the plurality of health statuses.

The instant invention further includes a method, performed by a computer-controlled apparatus, for submitting acoustical cardiovascular data to a central database. The method comprises the steps of: (1) receiving, from a user, a request to detect a cardiovascular signal of the user; (2) initializing a cardiovascular monitoring device connected to a computer in response to the request; (3) measuring the cardiovascular signal during a startup routine performed by the computer; (4) receiving, at the computer, at least a portion of the detected cardiovascular signal of the user; and (5) transmitting data based on the received cardiovascular signal to a central database for storage in a record corresponding to the user.

The methods and apparatus of the instant invention are contemplated to preferably include the use of an electret transducer as disclosed in U.S. Pat. No. 4,598,590 issued to Busch-Vishniac et al. on Jul. 8, 1986, and to incorporate the method of detecting cardiovascular signals, known as wide-band external pulse monitoring, as disclosed in U.S. Pat. No. 5,913,826 issued to Blank on Jun. 22, 1999, both of which are incorporated herein by reference. This device may yield more accurate results than traditional measurements using blood pressure cuffs, which are subject to human error.

In a particular embodiment, an electret transducer may be connected to a personal computer (PC) and used by a patient to measure her blood pressure. The electret transducer is activated during the startup routine performed by the PC when power to the PC is turned on. Upon completion of the startup routine, the resulting health statistic is transferred, preferably automatically, to the PC and then may further be transferred to a centrally-located computer. There, the results may be analyzed to determine a health status which is stored in a database used in conjunction with the instant invention.

The methods and accompanying apparatus are further contemplated to be used in conjunction with measuring a health statistic known as a "real age factor." A suitable method for determining a real age factor is disclosed by, for example, RealAge.com located on the Internet at a website bearing the same name. The method is further disclosed in a book entitled "Real Age—are You As Young As You Can Be" by Dr. Michael F. Roizen, M.D. In accordance with the invention, it is contemplated that a patient's real age factor is initially determined by, for example, a patient's responses to a questionnaire concerning the patient's physical and mental health, as well as personal habits, environmental influences and other factors which have been recognized as affecting aging. The patient's resulting health status will be modified whenever a new blood pressure measurement has been entered and stored in the patient's database record. Furthermore, it is contemplated that normative statuses relating to the monitored population as a whole will be changed by each individual entry and that such statistics can be updated in real time.

One advantage of the present invention lies with the ability to monitor and update both individual patient's health statistics as well as population statistics for all users that submit health statistics to the system. Such statistics may further be monitored and analyzed in real time.

A further advantage is that physicians, insurance companies and medical researchers, along with other interested parties, may access the information. The system of the present invention may provide unlimited access to certain parties, such as treating physicians, or may only provide certain information to other parties, such as researchers, while concealing an identity (in particular, a name or other identifying information) of a patient, thereby preserving her privacy. Insurance companies may receive statistical information for the population to determine health care premiums and the like, the computation of which is dependent on population-wide health data. However, access to information specific to a person may be denied to preserve privacy and to avoid health-based discrimination in the purchasing of health insurance.

A still further advantage is that fees may be charged for the provision or use of monitoring equipment, for submissions of data to the database or for use of information from the database, so as to fund the establishment, preservation and/or augmentation of the disclosed system.

BRIEF DESCRIPTION OF THE DRAWINGS

Further aspects of the instant invention will be more readily appreciated upon review of the detailed description of the preferred embodiments included below when taken in conjunction with the accompanying drawings, in which.

DETAILED DESCRIPTION OF THE PREFERRED EMBODIMENTS

Referring now to FIGS. 1 through 3B, wherein similar or identical components of the instant invention are referenced in like manner, preferred methods and accompanying apparatus for online health monitoring are disclosed.

Figure 1:
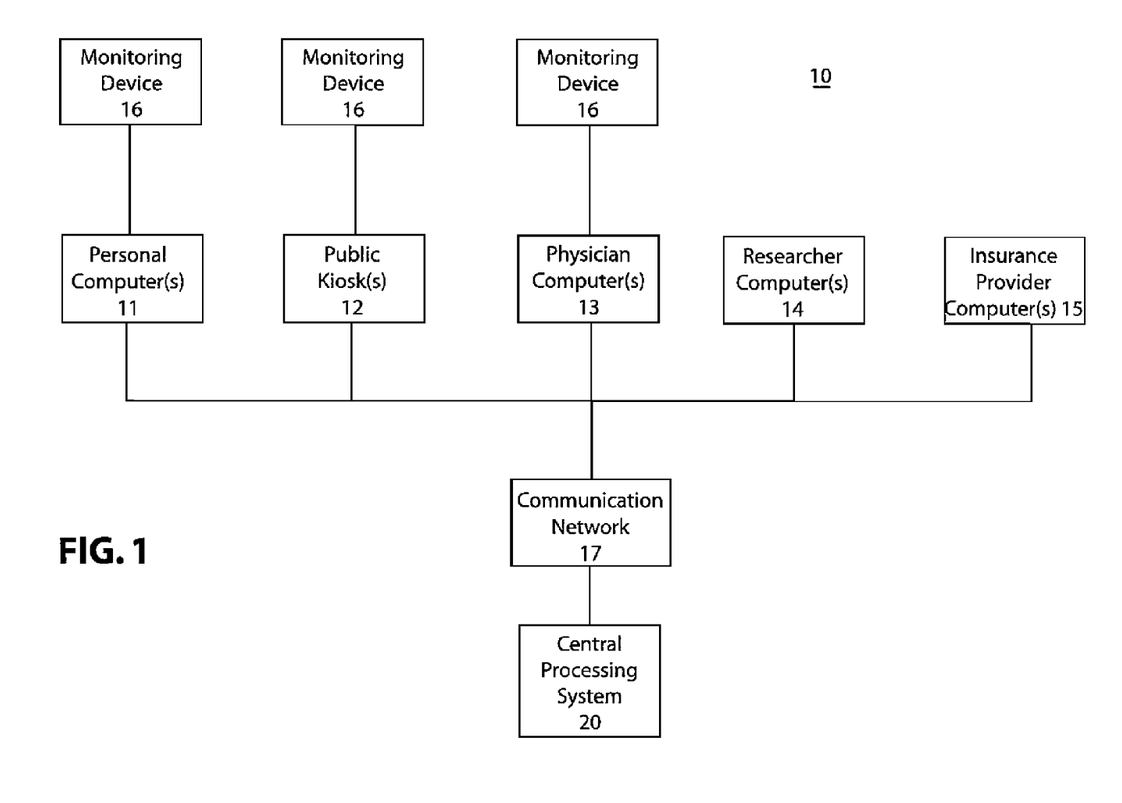
FIG. 1 is a schematic block diagram of a network for use with the instant invention.

FIG. 1 depicts a networked system 10 for use with the present invention. System 10 preferably includes a communication network 17 for transmitting data between a central processing system 20 and personal computer(s) 11, public kiosk(s) 12, physician computer(s) 13, researcher computer(s) 14 and insurance provider computer(s) 15. Personal computer(s) 11, public kiosk(s) 12 and physician computer(s) 13, in turn, are each preferably connected to a health monitoring device 16.

Communication network 17 may be any type of connection operable to transmit data between the central processing system 20 and the computers 11-15. Thus, the communication network 17 may be any one or more of a local area network, a wide area network, an electronic bulletin board system, a telecommunications line and the Internet.

Computers 11-15 may be any computing device operative to receive data from a user and/or a monitoring device 16 and to transmit and receive data through communication network 17 in conjunction with central processing system 20. The computing device may also be capable of performing certain calculations in storing data. In particular, personal computer(s) 11 are preferably one or more home personal computers owned or operated by persons who wish to have their health monitored by system 10.

Public kiosk(s) 12 are one or more freestanding public displays which include computer devices operative to receive data from a user and/or a monitoring device 16 and to transmit and receive data through communication network 17 in conjunction with central processing system 20. In one embodiment of the instant invention, it is contemplated that in order to promote public awareness, freestanding kiosks 12 will be placed in public areas such as shopping malls, amusement parks, fairgrounds, transportation terminals, and the like, so that members of the public may submit their personal and medical information and receive, inter alia, hypertension screening by submitting to a test using monitoring device 16 in operative connection with kiosk 12.

Physician computer(s) 13 are preferably one or more computing devices operative to receive data from a patient visiting a physician and/or from monitoring device 16 and to transmit and receive data through communication network 17 in conjunction with central processing system 20. In one embodiment of the instant invention, patients may submit their personal and medical information as well as submit to hypertension screening using monitoring device 16 while visiting his or her treating physician. The physician may store the data locally on physician computer(s) 13 and/or on central processing system 20 and may retrieve such information as required for purposes of diagnosis and treatment.

Researcher computer(s) 14 are and insurance provider computer(s) 15 are preferably operative to retrieve data from central processing system 20 through communication network 17. It is contemplated that researchers in the medical field may want access to health statistics compiled by system 10 in order to monitor the health of an individual or the population at large. In the case of insurance providers, it is contemplated that they may want access to such information in order to determine, inter alia, thresholds for health risks in determining premiums for providing health care insurance. Thus, access to collected information may be provided to these groups as well as others not specifically mentioned. Access to the information may be provided either for free or for a fee. Access may furthermore be provided on a subscriber basis or on a transaction-by-transaction basis. In addition, access to individual records may be provided to these and other entities while maintaining the anonymity of the individual submitting the information and/or suppressing any other submitted information as desired.

Health monitoring device 16 may be an electret transducer or foil electret transducer as described above and as set forth in more detail in U.S. Pat. No. 5,913,826. However, it is further contemplated that the health monitoring device may also be any acoustic or other device for detecting blood pressure and which may transfer data to a computer 11-13 or central processing system 20.

Figure 2:
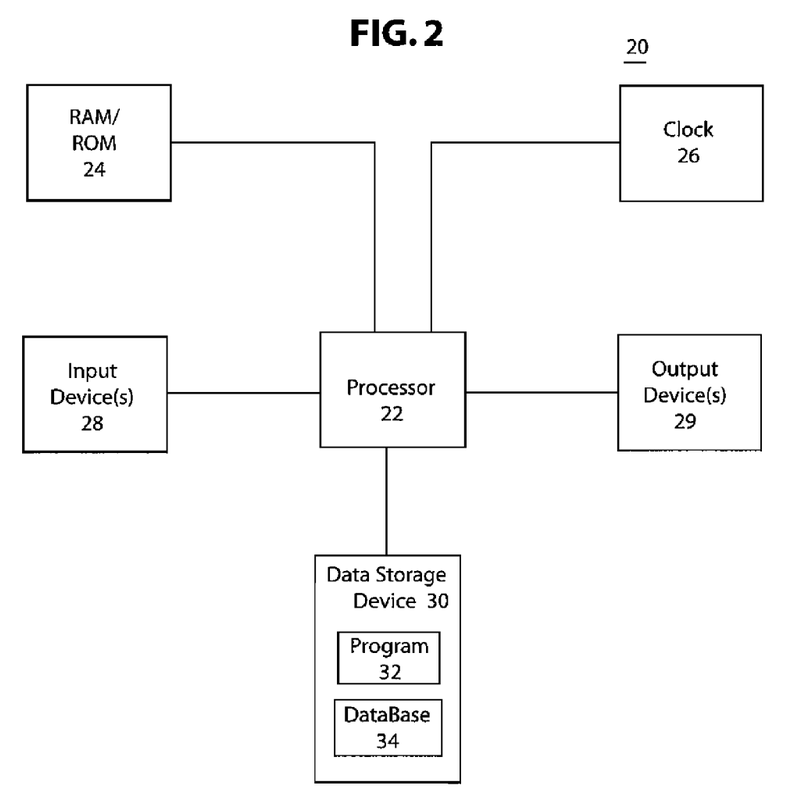
FIG. 2 is a schematic block diagram of the central processing system of the instant invention.

Turning now to FIG. 2, depicted therein is the central processing system (CPS) 20. CPS 20 is operative to receive program instructions and user inputs, and is further operative to output results corresponding to such instructions and inputs, in accordance with the present invention. CPS 20 comprises a processor 22 which may be any commonly available microprocessor such as the PENTIUM III manufactured by INTEL CORP. Processor 22 is operatively connected to RAM/ROM 24, clock 26, data storage device 30 (which stores program 32 and database 34), input device(s) 28 and output device(s) 29.

The random-access memory (RAM) portion of RAM/ROM 24 may be a suitable number of Single In-line Memory Module (SIMM) chips having a storage capacity (typically measured in kilobytes or megabytes) sufficient to store and transfer, inter alia, processing instructions utilized by processor 22 and received from program 32 during the operation of central processing system 20. The read-only memory (ROM) portion of RAM/ROM 24 may be any permanent non-re-writable memory medium capable of storing and transferring, inter alia, processing instructions performed by processor 22 during a start-up routine of central processing system 20. Further functions of RAM/ROM 24 will be apparent to one of ordinary skill in the art.

Clock 26 may be an on-board component of processor 22 which dictates a clock speed (typically measured in MHz) at which processor 22 performs and synchronizes, inter alia, communication between hardware components of central processing system 20. Further functions of clock 26 will be apparent to one of ordinary skill in the art.

Input device(s) 28 may be one or more commonly known devices, which may be used for communicating information to central processing system 20 via either another computer system or by user inputs. Accordingly, input device(s) 28 may include a keyboard, a mouse, a graphics tablet, a scanner, a voice recognition unit, a parallel or serial communication port, a modem, a network connection and any appropriate network or other communication card for receiving data. Input device(s) 28 is/are operative to allow a user to input instructions and values in accordance with the present invention.

Output device(s) 29 may be one or more commonly known devices, which may be used by central processing system 20 to communicate the results of input instructions and values to a user of the central processing system 20. Accordingly, output device(s) 29 may include a display monitor, a voice synthesizer, a printer, a parallel or serial communication port, a modem, a network connection and any appropriate network or other communication card for sending data. Output device(s) 29 is/are operative to allow a user to receive the results of input instructions and values in accordance with the present invention.

Data storage device 30 may be an internal or external large capacity memory for storing computer data, the storage capacity of which is typically measured in megabytes or gigabytes. Data storage device 30 stores, inter alia, an operating system (not shown) such as WINDOWS NT by MICROSOFT CORP, and one or more application programs, such as program 32 and database 34. Accordingly, data storage device 30 may be one or more of the following: a floppy disk drive, a hard disk drive, a CD-ROM disk and reader/writer, a DVD disk and reader/writer, a ZIP disk and a ZIP drive of the type manufactured by IOMEGA CORP., and/or any other computer readable medium that may be encoded with processing instructions in a read-only or read-write format. Further functions of, and available devices for, data storage device 30 will be apparent to one of ordinary skill in the art.

Program 32 includes a plurality of processing instructions which enables central processing system 20 to receive inputs of data and information in accordance with the present invention. Program 32 may be written in any conventional computer language that is comprehensible to central processing system 20, such as C++, Visual Basic, or the like.

Program 32 is operative to interpret raw data received from health monitoring device 16, such as an electret transducer and a foil electret transducer. In particular, the health statistics of a user received from a health monitoring device may include one or more waveforms indicative of a user's blood pressure. Program 32 may perform K1, K2 and K3 waveform analysis as disclosed in U.S. Pat. No. 5,913, 826 to Blank, which is incorporated herein by reference. These analyses include performing one or more of analyzing shapes of the waveforms, slopes of the waveforms, areas under the curve of the waveforms and timing of these events to measure arterial pressure, arterial pressure over time, blood flow, arterial elasticity, and the like. As a result of these analyses, an overall cardiac condition of the patient, including cardiac output, which may be used in conjunction with the instant invention.

Figure 3A:
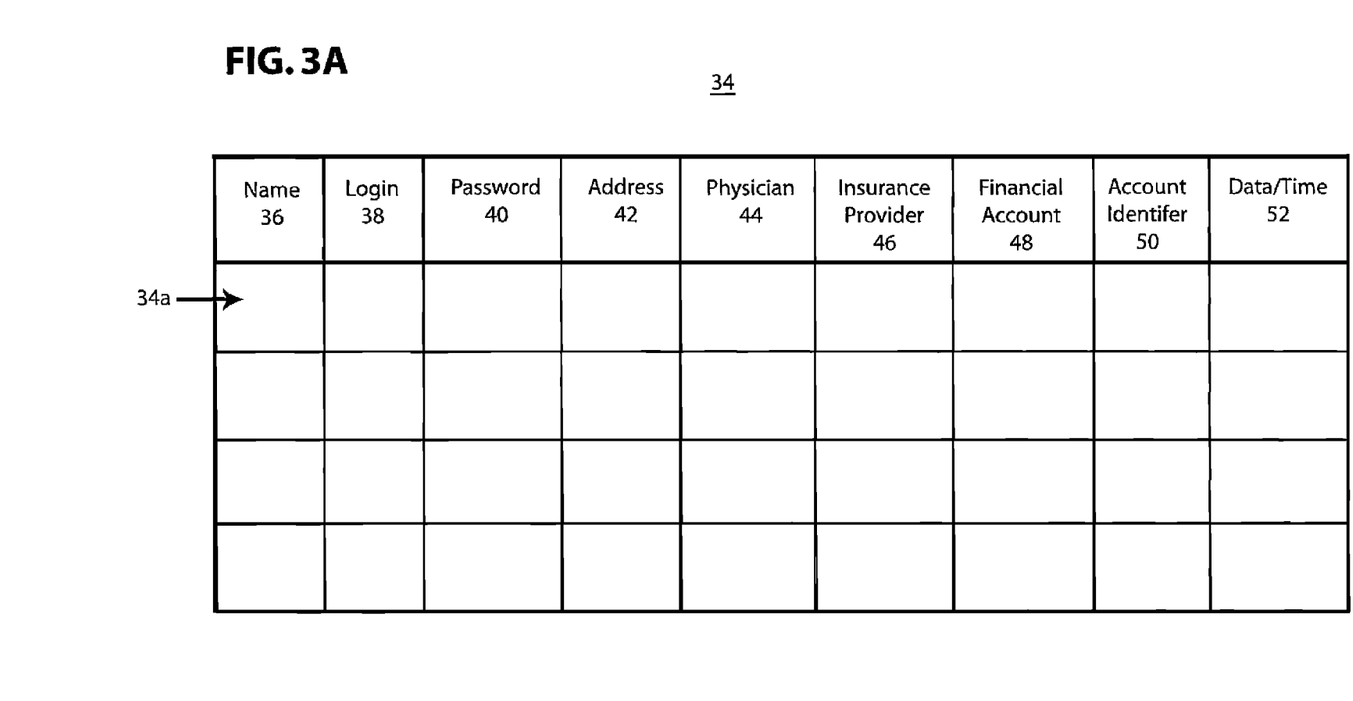
FIG. 3A is a diagram illustrating an exemplary database containing user identification data which is used in conjunction with the instant invention.
Figure 3B:
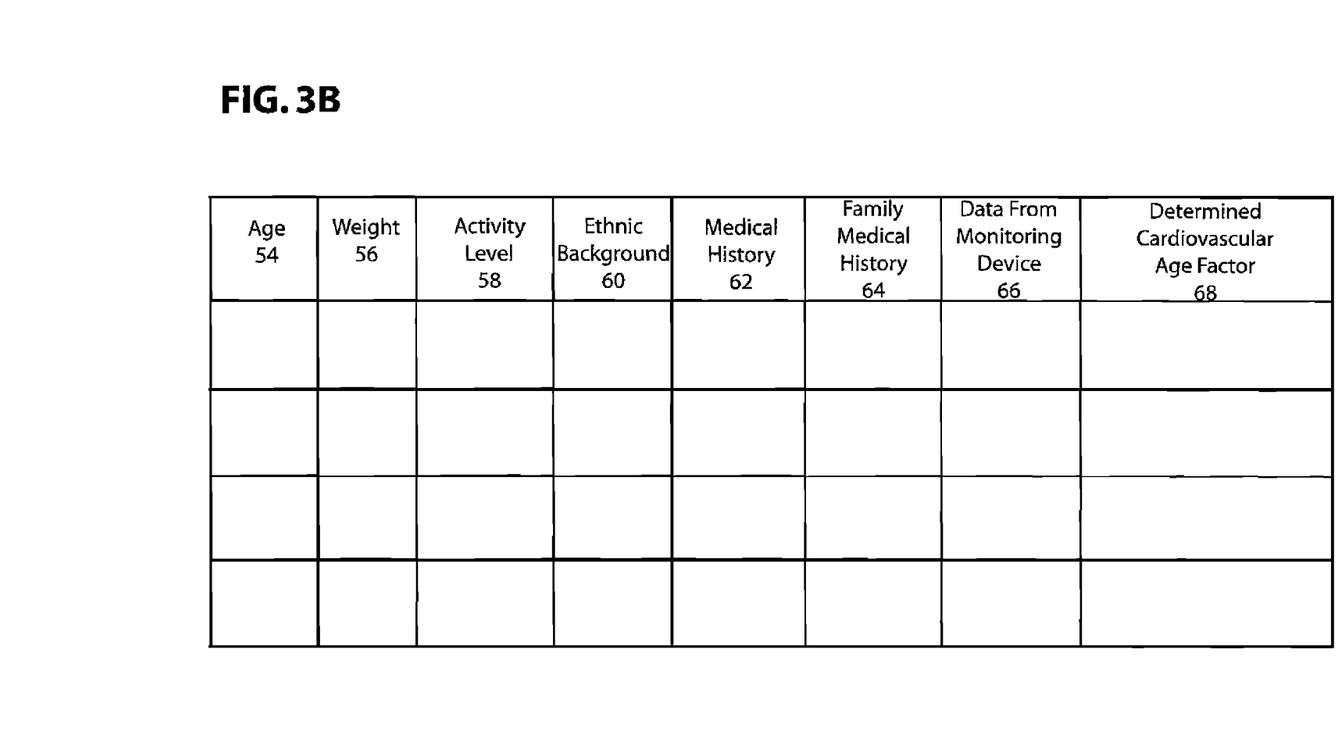
FIG. 3B is a diagram illustrating an exemplary database containing user medical data which is used in conjunction with the instant invention.

From this information, and in conjunction with the data stored in fields 54-68 of database 34, program 32 is further operative to determine a user's cardiovascular age factor or "real age factor," also referred to herein as a health status. This health status is a numeric indication resulting from a statistical comparison of the analyses described immediately above for the user and statistics derived from analyses of all users who have submitted their health statistics to system 10. In particular, program 32 is operative to determine a mean figure for cardiovascular health and standard deviations from the mean for the plurality of users. The health statistic of an individual is then compared to the mean figure. The health status of the user may then be determined according to the number of standard deviations the user's health statistic is from the mean figure. Factors such as a person's age, weight, activity level, ethnic background, medical history and family medical history may be used to refine the health status of the individual, as will be apparent to one of ordinary skill in the art.

The health status, once determined, may then be used to diagnose a hypertensive condition of the user and to determine any necessary course of treatment, including prescribing further tests such as an angiogramme. In addition, as each user submits their information and health statistics, the system more accurately describes the health condition of the population at large and may provide researchers, insurance providers and the like with a real time view of the same.

In lieu of receiving raw data, as described above, program 32 is also operative to receive waveform analyses performed by one of computers 11-13, provide a statistical comparison to the plurality of users and to store the analyzed information in a user record. Thus, it is contemplated that the waveform analyses may be performed locally at computers 11-13 or centrally by CPS 20.

Database 34 may be any commonly available database program such as ORACLE, and is preferably any high-level SQL-based database program operative to receive, maintain and output data for a suitable number of users for fields 36-68, which are described further below.

FIGS. 3A and 3B illustrate exemplary fields which may be included in a database 34 used by CPS 20 to track individual and population-wide health statistics and statuses. Each user submission is stored in a record 34a, which is represented by one row of FIGS. 3A and 3B.

Database 34 preferably contains name field 36, login ID field 38, password field 40, address field 42, physician field 44, insurance provider field 46, financial account field 48, account identifier field 50, date/time field 52, age field 54, weight field 56, activity level field 58, ethnic background field 60, medical history field 62, family medical history field 64, data from monitoring device field 66 and determined cardiovascular age factor field 68.

Name field 36 preferably stores a users name or other definitive identifying data such as a social security number, driver's license number or the like. Upon a user's request, this information may be suppressed when third parties perform research using database 34.

Login ID 38 is a unique login identification that a user uses when submitting health statistics and information or when searching database 34. The login ID may be any alpha, numeric or alphanumeric sequence and may furthermore be selected by the user or assigned by CPS 20.

Password field 40 contains any alpha, numeric or alphanumeric sequence that a user must input to verify his identity upon attempting to access database 34. If desired, a user may provide his login ID and password to an attending physician so that he or she may access the user's records.

Address field 42 preferably contains an address of the user but may contain any other contact information such as a post office box number, a work address, a telephone number, or an e-mail address where the user may be reached.

Physician field 44 preferably contains a name and contact information for a treating physician for the user. It may also contain the names of physicians authorized to access the user's information.

Insurance provider field 46 preferably contains the name, contact information and/or policy information of a user's health insurance provider. It is contemplated that a health insurance provider may pay for the instant service and/or would want access to the information concerning their insureds. Thus, field 46 has been provided so that an insurance provider may be contacted for payment or may receive the health information they require.

Financial account field 48, in conjunction with account identifier field 50, is included so that a fee for the service may be charged against a user's financial account such as a credit card, a banking account or an online digital cash account. In one embodiment, a user may be charged a fee for submitting or accessing information. In the alternative, fields 48 and 50 may list an insurance provider if the fee is to be paid by that entity.

Date/time field 52 contains a date and or a time that a user has submitted health statistics and information. Thus, a history for the user may be generated based on each submission the user provides. Date/time field 52 will then be used to sort the user's information into chronological order.

Age field 54 preferably contains an age of the user or an age group to which the user belongs. Likewise, weight field 56 preferably contains a weight of the user or a weight group to which the user belongs. The height of the user may also be stored in this field or in a separate field (not shown).

Activity level field 58 preferably describes a user's physical activity level, such as the amount of times per week the user exercises and the like.

Ethnic background field 60 preferably contains a description of the ancestry of the user which may be useful in predicting dispositions to certain health conditions.

Medical history field 62 preferably contains a list of maladies or conditions that the user has suffered in the past which may be useful in predicting dispositions to certain health conditions and in prescribing treatments.

Family medical history field 64 preferably contains a list of maladies or conditions known to have been suffered by any of the user's blood relatives. This information may be useful in predicting dispositions to certain health conditions.

Data from monitoring device field 66 preferably contains the raw or pre-analyzed data received from the monitoring device 16 over the communication network 17. In the alternative, field 66 may contain a pointer to another file location in the data storage device 30 where such data may be stored.

The determined cardiovascular age field 68 preferably contains the determined cardiovascular age factor for the user, derived in the manner described above in conjunction with program 32.

Further fields or fewer fields may be used in accordance with this invention, as will be apparent to one of ordinary skill in the art.

Additional embodiments may be used separately or in conjunction with the invention as described above. In particular, it is contemplated that measurements rom a health monitoring device may be used in determining a cardiovascular or real age factor. Population statistics may be compiled from individual statistics and statuses. Measurements of a patient's health statistics may be made by a health monitoring device during a startup routine performed by an attached personal computer, or the like. Fees may be charged for accessing information from or storing information in the database, as well as for using or purchasing an apparatus for use in health monitoring. Individual user's privacy may be maintained by blocking access by certain parties to stored patient identifying information. Access to the database may be accomplished via the Internet, direct modem access, and the like. Other variations of the instant invention may also be apparent to one of ordinary skill in the art.

In an illustrative arrangement, monitoring devices 16 are sold to physicians or leased to them for use with their patients in providing accurate measurements of arterial pressure, blood flow, elasticity and the like. These devices 16 would induce a data entry means and a connection to processor 22, e.g., over the Internet. In a sale or lease situation, the patient could be charged a fee for a test with the device. This fee would entitle the patient not only to the test results, but a file or record on the database 34 and access to it, e.g., via the Internet. A lesser fee could be charged for subsequent tests with the device 16.

During the test in the physician's office, information about the patient, e.g., as represented by the fields shown in FIGS. 3A and 3B would be entered on device 16. Device 16 would automatically establish a connection with processor 22 and database 34, where the patient record would be created and the data stored. Processor 22 could also issue a login ID 38 and password 40 to the patient. This would be transmitted back to device 16 and given to the patient. The physicians office would also keep a record of this information in the patient's file, so the physician would have access to the information, especially when additional information is added subsequently.

During later visits to the physician the tests could be repeated and the patient's record on database 34 updated. In addition, the patient could periodically take the test at public kiosks 12 or could access his or her record at the kiosk for review. If the patient was feeling uneasy about his or her health condition, the kiosk could be used for a test on an "as desired" basis. Use of the kiosk would be on a fee basis to support the maintenance of the kiosk.

In addition to the kiosk, the patient may gain access to his records over the Internet using a standard PC equipped with a modem and web browser software. It is anticipated that this access would be without charge to the user. This would include access to the person's cardiovascular age, which the patient could track over time, seeing it decrease with exercise and medication or increase when a course of treatment is not followed.

The physician can also make entries in the patient's record, e.g., from device 16 in his office or a kiosk. This information may, for example, put limits on test results and instructions in case the limits are exceeded. In this regard the physician may require that whenever the patient's blood pressure exceeds 140/100, when the patient receives the results he is also instructed to call the physician. In addition or as an alternative, the physician may be notified by means of a message delivered to device 16 in his office to contact the patient and the reason the contact should be made. Further, the physician may routinely review the patient's record or may review it in anticipation of a visit. Such access to the database, may be on a fee basis which is charged to the patient. Similarly, the operator of the system may establish accounts and charge insurance companies and researchers for access to the database. The fees may be different, so that researchers connected with hospitals and universities are subsidized by commercial entities like insurance companies. As noted above, limitations may be placed on the amount of access by researchers and insurance companies.

Although the invention has been described in detail in the foregoing embodiments, it is to be understood that they have been provided for purposes of illustration only and that other variations both in form and detail can be made thereupon by those skilled in the art without departing from the spirit and scope of the invention, which is defined solely by the appended claims.

We claim:

1. A method, performed by a computer-controlled apparatus, for submitting acoustical cardiovascular data to a central database, the method comprising:
   receiving, from a user, a request to detect a cardiovascular signal of the user;
   initializing a cardiovascular monitoring device connected to a computer in response to the request;
   measuring an acoustical cardiovascular signal with the cardiovascular monitoring device while a startup routine performed by the computer is ongoing;
   analyzing a waveform of the cardiovascular signal to determine at least one of a shape of the signal, a slope of the signal, and an area under the signal; and
   receiving, at the computer after the startup routine, at least a portion of the detected cardiovascular signal of the user;
   transmitting data based on the received cardiovascular signal to a central database for storage in a record corresponding to the user;
   associating limits with the data based on the received cardiovascular signal; and
   notifying a user's physician, with a message sent from the computer, to contact the user when the limits are exceeded by the data.

2. The method of claim 1, wherein the step of receiving a request further comprises:
   receiving, from the user, user identification data corresponding to the user including at least one of: a name, an address, a login name, a password, a health care provider, a health insurance provider, a time that the request was generated, and a financial account identifier corresponding to a financial account;
   receiving user medical data corresponding to the user including at least one of: an age, a height, a weight, an activity level, an ethnic group, a medical history, and a family medical history; and wherein the transmitting step further comprises:
   transmitting at least a portion of one of the user identification data and the user medical data to the central database.

3. The method of claim 1, wherein the cardiovascular monitoring device comprises an electret transducer.

4. The method of claim 3, wherein the acoustical cardiovascular signal comprises acoustic data from the electret transducer, the acoustic data including at least one waveform.

5. The method of claim 4, wherein the analyzing step further comprises:
   measuring at least one of a shape of the waveform, a slope of the waveform, and an area under the waveform;
   determining a cardiovascular age factor of the user based on the measuring step; and
   storing the cardiovascular age factor in the database as the health statistic.

6. The method of claim 5, further comprising:
   providing the cardiovascular age factor to at least one of the user and a second user.

7. The method of claim 1, the method further comprising:
   determining a cardiovascular age factor of the user based on the measuring step; and wherein the transmitting step further comprises:
   transmitting the cardiovascular age factor to the central database.

8. The method of claim 1, wherein the transmitting step further comprises:
   transmitting the data to the central database through one of a modem connection and the Internet.

9. The method of claim 1, wherein the message contains information regarding a reason for contacting the user.

10. The method of claim 1 further including the steps of:
    establishing the database, under the control of a computer, for storing a plurality of health statuses of a plurality of users, wherein the database is centrally-accessible from the Internet;
    receiving, over the Internet, from a user, data corresponding to a health statistic of the user, the data generated by the cardiovascular monitoring device;
    analyzing the health statistic to determine a health status from the health statistic, wherein the analyzing step includes comparing data received from the cardiovascular monitoring device and statistics derived from analysis of the plurality of health statuses;
    storing the health status in the database;
    updating a population statistic based on the health status and the plurality of health statuses;
    associating limits with at least one health statistic received from the user; and
    notifying a user's physician, with a message sent from the computer, to contact the user when the limits are exceeded by the health statistic.

11. The method of claim 10, wherein the health statistic comprises cardiovascular data.

12. The method of claim 11, wherein the cardiovascular data corresponds to a blood pressure of the user.

13. The method of claim 10, wherein the receiving step further comprises:
    receiving, from the user, a request to store the data;
    receiving a financial account identifier corresponding to a financial account; and
    charging a fee against the financial account in response to the request.

14. The method of claim 10, further comprising:
    receiving, from a second user, second data corresponding to a health statistic of the second user.

15. The method of claim 10, further comprising:
    receiving, from the user, second data corresponding to the health statistic of the user at a separate time;
    analyzing the second data to generate a second health statistic of the user; and
    storing the second health statistic of the user.

16. The method of claim 10, wherein the health status is the user's cardiovascular age factor.

17. The method of claim 10, wherein the message contains information regarding a reason for contacting the user.

18. The method of claim 10, wherein the analyzing step further includes statistically comparing data received from the health monitoring device and statistics derived from analysis of the plurality of health statuses of the plurality of users.

19. The method of claim 10, wherein the receiving step further comprises:
- receiving user identification data corresponding to the user including at least one of: a name, an address, a login name, a password, a health care provider, a health insurance provider, a time that the first data was generated, and a financial account identifier corresponding to a financial account; and
- receiving user medical data corresponding to the user including at least one of: an age, a height, a weight, an activity level, an ethnic group, a medical history, and a family medical history.

20. The method of claim 19, wherein the storing step further comprises:
- storing the user identification data and user medical data in the database.

21. The method of claim 19, wherein the analyzing step further comprises:
- determining a cardiovascular age factor of the user based on the data and at least a portion of the user medical data; and
- storing the cardiovascular age factor in the database.

22. The method of claim 21, further comprising:
- providing the cardiovascular age factor to at least one of the user and a second user.

23. The method of claim 10, further comprising:
- receiving, from a second user, a request for the health status; and
- providing the health status to the second user.

24. The method of claim 23, wherein the providing step further comprises:
- receiving, from the second user, a financial account identifier corresponding to a financial account; and
- charging a fee to the financial account in response to the request.

25. The method of claim 23, wherein the health status is provided and an identity of the first user is withheld.

26. The method of claim 23, further comprising:
- determining a plurality of population health statistics from the plurality of health statuses, including the first health status.

27. The method of claim 26, further comprising:
- receiving, from a second user, a request for at least a portion of the population health statistics; and
- providing the requested portion of population health statistics to the second user.

28. The method of claim 27, wherein the providing step further comprises:
- receiving a financial account identifier corresponding to a financial account; and
- charging a fee against the financial account, in response to the request.

* * * * *